US011422076B1

United States Patent
Zhang et al.

(10) Patent No.: US 11,422,076 B1
(45) Date of Patent: Aug. 23, 2022

(54) K-NEAREST NEIGHBOUR ROCK BURST PREDICTION METHOD AND DEVICE BASED ON BIG DATA VISUALIZATION ANALYSIS

(71) Applicant: Beijing University of Civil Engineering and Architecture, Beijing (CN)

(72) Inventors: Yu Zhang, Beijing (CN); Mingkui Zhang, Beijing (CN); Dongqiao Liu, Beijing (CN); Maozu Guo, Beijing (CN); Jitao Li, Beijing (CN); Zhaoyong Lv, Beijing (CN); Yilin Su, Beijing (CN); Kailong Gao, Beijing (CN); Kaifeng Liu, Jiangsu (CN)

(73) Assignee: BEIJING UNIVERSITY OF CIVIL ENGINEERING AND ARCHITECTURE, Beijing (CN)

( * ) Notice: Subject to any disclaimer, the term of this patent is extended or adjusted under 35 U.S.C. 154(b) by 0 days.

(21) Appl. No.: 17/681,221

(22) Filed: Feb. 25, 2022

(30) Foreign Application Priority Data

Jun. 4, 2021 (CN) .......................... 202110621619.4

(51) Int. Cl.
 *G01N 3/08* (2006.01)
 *G06F 17/14* (2006.01)
 *G01N 33/24* (2006.01)
(52) U.S. Cl.
 CPC .............. *G01N 3/08* (2013.01); *G01N 33/24* (2013.01); *G06F 17/141* (2013.01)
(58) Field of Classification Search
 CPC ......... G01N 3/08; G01N 33/24; G06F 17/141
 See application file for complete search history.

(56) References Cited

FOREIGN PATENT DOCUMENTS

| CN | 111123355 A | | 5/2020 | |
|---|---|---|---|---|
| CN | 113076700 A | * | 7/2021 | |
| WO | WO-2018170035 A1 | * | 9/2018 | .......... E21B 49/003 |

OTHER PUBLICATIONS

CNIPA, Notification of a First Office Action: Appl. No. CN 202110621619.4, dated Jul. 16, 2021.
Beijing University of Civil Engineering and Architecture , Response to Notification of a First Office Action: Appl. No. CN 202110621619.4 and replacement Claims, Jul. 26, 2021.
CNIPA, Notification to grant patent right for invention: Appl. No. CN 202110621619.4, dated Sep. 3, 2021.
Su Guo-shao, Zhang Xiao-fei, Yan Liu-bin, "Rockburst Prediction Method Based on Case Reasoning Pattern Recognition", Journal of Mining & Safety Engineering, Mar. 2008, pp. 63-67, vol. 25 No. 1.

* cited by examiner

*Primary Examiner* — Jonathan M Dunlap
(74) *Attorney, Agent, or Firm* — Hemisphere Law, PLLC; Zhigang Ma

(57) ABSTRACT

A K-nearest neighbour rock burst prediction method and device based on big data visualization analysis are provided. The method includes the following steps: S1, obtaining spectrum characteristics and amplitude/energy characteristics of rocks according to rock data; and S2, accurately predicting rock burst by a K-nearest neighbour algorithm according to the spectrum characteristics and the amplitude/energy characteristics. By adopting the technical scheme, the rock burst can be accurately predicted to avoid huge economic and casualties.

4 Claims, 1 Drawing Sheet

K-NEAREST NEIGHBOUR ROCK BURST PREDICTION METHOD AND DEVICE BASED ON BIG DATA VISUALIZATION ANALYSIS

TECHNICAL FIELD

The invention belongs to the technical field of rock burst prediction, and in particular to K-nearest neighbour rock burst prediction method and device based on big data visualization analysis.

BACKGROUND

When the rock mass engineering enters the deep part, due to the joint influence of high ground stress, high ground temperature, high water pressure and engineering disturbance factors, in some underground works such as coal mines, underground hydropower stations, deep-buried tunnels and diversion tunnels, the wall rock will be suddenly and violently destroyed, with the rapid release of energy at the same time. This kind of destruction of rock mass is usually called rock burst. The scale of rock burst is huge. Moreover, rock burst not only seriously affects production, but also causes equipment damage, casualties and incalculable economic losses. At present, it is not possible to accurately predict rock burst to avoid huge economic and personnel losses.

SUMMARY

A technical solution of the invention is to provide K-nearest neighbour rock burst prediction method and device based on big data visualization analysis, which can accurately predict rock burst to avoid huge economic and personnel losses.

To achieve the above objective, the invention adopts the following technical scheme:

a K-nearest neighbour rock burst prediction method based on big data visualization analysis including S1, obtaining spectrum characteristics and amplitude/energy characteristics of rocks according to rock data;

and S2, accurately predicting rock burst by the K-nearest neighbour algorithm according to the spectrum characteristics and the amplitude/energy characteristics.

Preferably, S1 specifically includes:

step 11, acquiring the rock data;

step 12, performing Fourier transform on time domain data of the rock data to obtain frequency domain data of the rock data; and step 13, according to the frequency domain data of the rock data, extracting the spectrum characteristics and the amplitude/energy characteristics of the rock data.

Preferably, in step 12, obtaining frequency domain data of the rock data includes:

sub-step 121: parsing the rock data;

sub-step 122, extracting the parsed waveform file data, and sorting the waveform file data according to a time sequence of rock burst occurrence; and sub-step 123: performing fast Fourier transform on the sorted waveform file data to obtain frequency domain-amplitude values, that is, the frequency domain data of the rock data.

Preferably, S2 specifically includes:

step 21, acquiring the spectrum characteristics and the amplitude/energy characteristics of rock data; and step 22, according to the spectrum characteristics and the amplitude/energy characteristics, accurately predicting the rock burst by the K-nearest neighbour algorithm.

Preferably, in the step 13, extracting the spectrum characteristics of the rock data includes:

sub-step 1311, obtaining real-time times of occurrence time of rock burst according to the frequency domain data of the rock data, and storing the real-time times in a "Dominant frequency.TXT" file in turn; in the "Dominant frequency.TXT" file, a first column is the real-time times of occurrence time of rock burst, a second column is maximum dominant frequency values extracted from a whole rock burst process by fast Fourier transform, and a third column is maximum amplitude values extracted from the whole rock burst process by fast Fourier transform;

sub-step 1312: taking a time series in the first column of the "Dominant frequency.TXT" file as the X axis and a dominant frequency series in the second column of the "Dominant frequency.TXT" file as the Y axis, and making a scatter plot to obtain a dominant frequency distribution map/chart;

sub-step 1313: analyzing data of the "Dominant frequency.TXT" file to a median dominant frequency of about 84.472 KHz and an average dominant frequency of about 134.410 KHz;

sub-step 1314, according to the dominant frequency distribution map, dividing dominant frequencies into five dominant frequency bands, the five dominant frequency bands respectively are a low frequency band with dominant frequencies less than 50 KHz, a medium-low frequency band with dominant frequencies greater than or equal to 50 KHz and less than 150 KHz, a medium frequency band with dominant frequencies greater than or equal to 150 KHz and less than 250 KHz, a medium-high frequency band with dominant frequencies greater than or equal to 250 KHz and less than 350 KHz, and a high frequency band with dominant frequencies greater than 350 KHz; among them, there are 203 numbers of dominant frequencies less than 50 KHz, 18464 numbers of dominant frequencies at 50 KHz-150 KHz, 1149 numbers of dominant frequencies at 150 KHz-250 KHz, 5678 numbers of dominant frequencies at 250 KHz-350 KHz, and 459 numbers of dominant frequencies greater than 350 KHz; and after calculating a number ratio of the five dominant frequency bands, visualizing a pie chart of dominant frequency distribution of the rocks; and sub-step 1315: obtaining a spectrum rule of rock burst according to the dominant frequency distribution map, the median dominant frequency, the average dominant frequency and the pie chart of dominant frequency distribution.

Preferably, in step 2, according to the "Dominant frequency.TXT" file that the first column is the real-time times of occurrence time of rock burst, the second column is the maximum dominant frequency values extracted from the whole rock burst process by fast Fourier transform and the third column is the maximum amplitude values extracted from the whole rock burst process by fast Fourier transform, standardizing the maximum dominant frequency values in the second column and the maximum amplitude values in the third column in the "Dominant frequency.TXT" file as per a formula to thereby normalize as data of 0-1, and the formula is as follows:

$$X^* = \frac{X - X_{min}}{X_{max} - X_{min}},$$

in which: X is a desired characteristic value, X* is a standardized value of the desired characteristic value, $X_{min}$ is a minimum value in a characteristic class, and $X_{max}$ is a maximum value in the characteristic class.

On the basis of data normalization, dominant frequency and amplitude data of acoustic emission are used as input characteristic data, and results of indicating rock burst occurred or not obtained by automatic identification are used as classification labels, that is, labels of data in the occurrence time of rock burst during a process of rock burst experiment are taken as 1, and labels of the other data in the time of without rock burst are taken as 0.

The invention also provides a K-nearest neighbour rock burst prediction device based on big data visualization analysis, including:

an extraction module, which is used for obtaining the spectrum characteristics and amplitude/energy characteristics of rocks according to rock data; and and a prediction module, which is used for accurately predicting the rock burst through the K-nearest neighbour algorithm according to the spectrum characteristics and the amplitude/energy characteristics. In an exemplary embodiment, the extraction module and the prediction module are software modules stored in one or more memories and executable by one or more processors coupled to the one or memories to carry out any one of the above described K-nearest neighbour rock burst prediction methods.

According to the rock data, the invention obtains the spectrum characteristics and amplitude/energy characteristics of the rock; according to the spectrum characteristics and amplitude/energy characteristics, the invention accurately predicts the rock burst by K-nearest neighbour algorithm. By adopting the technical scheme of the invention, the rock burst can be accurately predicted to avoid huge economic and casualties.

BRIEF DESCRIPTION OF DRAWINGS

In order to more clearly explain the embodiments of the invention or the technical solutions in the prior art, the following will briefly introduce the drawings that need to be used in the description of the embodiments or the prior art. Obviously, the drawings in the following description are only some embodiments of the invention, and for ordinary technicians in the field, other drawings may be obtained according to these drawings without paying any creative efforts.

DETAILED DESCRIPTION OF EMBODIMENTS

Figure 1:
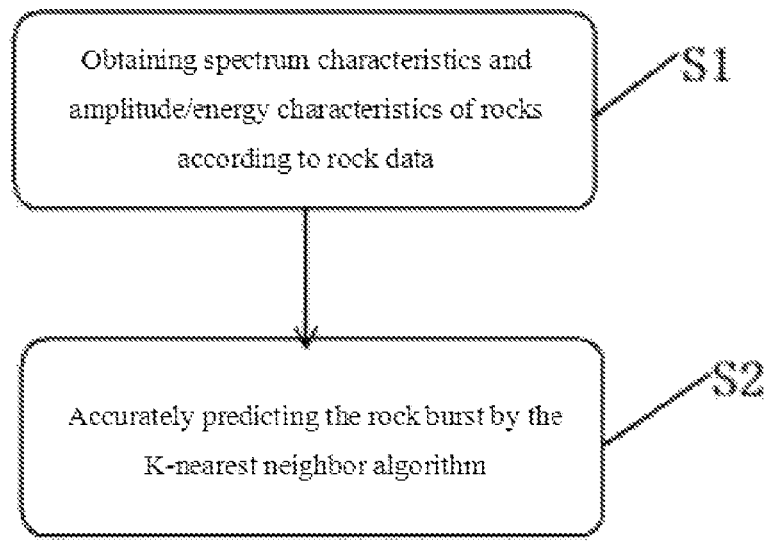
FIG. 1 is a flow chart of the K-nearest neighbour rock burst prediction method based on big data visualization analysis according to the invention.

In the following embodiments, the invention will be described in detail with reference to the drawings. In the drawings or descriptions, similar or identical parts use the same reference numerals, and in practical application, the shape, thickness or height of each part can be expanded or reduced. The embodiments of the invention are only used to illustrate the invention instead of limiting the scope of the invention. Any obvious modifications or changes to the invention do not depart from the spirit or scope of the invention.

As shown in FIG. 1, the invention provides a K-nearest neighbour rock burst prediction method based on big data visualization analysis, including:

S1, obtaining spectrum characteristics and amplitude/energy characteristics of rocks according to rock data;

and S2, accurately predicting rock burst by the K-nearest neighbour algorithm according to the spectrum characteristics and the amplitude/energy characteristics.

Further, S1 specifically includes:

step 11, acquiring the rock data;

step 12, performing Fourier transform on time domain data of the rock data to obtain frequency domain data of the rock data; and step 13, according to the frequency domain data of the rock data, extracting the spectrum characteristics and the amplitude/energy characteristics of rock data;

further, in the step 12, obtaining frequency domain data of the rock data includes:

sub-step 121: parsing/analyzing the rock data (to obtain parsed waveform file data);

sub-step 122, extracting the parsed waveform file data, and sorting the waveform file data according to the time sequence of rock burst occurrence; and sub-step 123: performing fast Fourier transform on the sorted waveform file data to obtain the frequency domain-amplitude values, that is, the frequency domain data of rock data.

Further, in the step 13, extracting the spectrum characteristics of the rock data includes:

sub-step 1311, obtaining real-time times of occurrence time of rock burst according to the frequency domain data of the rock data, and storing the real-time times in the "Dominant frequency.TXT" file in turn; in the "Dominant frequency.TXT" file, a first column is the real-time times of occurrence time of rock burst, a second column is maximum dominant frequency values extracted from a whole rock burst process by fast Fourier transform, and a third column is maximum amplitude values extracted from the whole rock burst process by fast Fourier transform;

sub-step 1312: taking a time series of the first column of the "Dominant frequency.TXT" file as the X axis and a dominant frequency series in the second column of the "Dominant frequency.TXT" file as the Y axis, and making a scatter plot to obtain a dominant frequency distribution map;

sub-step 1313: analyzing the data of "Dominant frequency.TXT" file, and finding a median dominant frequency of about 84.472 KHz and an average dominant frequency of about 134.410 KHz;

sub-step 1314, according to the dominant frequency distribution map, dividing the dominant frequencies into five dominant frequency bands, which are respectively a low frequency band with dominant frequencies less than 50 KHz, a medium-low frequency band with dominant frequencies greater than or equal to 50 KHz and less than 150 KHz, a medium frequency band with dominant frequencies greater than or equal to 150 KHz and less than 250 KHz, a medium-high frequency band with dominant frequencies greater than or equal to 250 KHz and less than 350 KHz, and a high frequency band with dominant frequencies greater than 350 KHz, and finding that there are 203 numbers of dominant frequencies less than 50 KHz (low frequency), 18464 numbers of dominant frequencies greater than or equal to 50 KHz and less than 150 KHz (medium and low frequency), 1149 numbers of dominant frequencies greater than or equal to 150 KHz and less than 250 KHz (medium frequency), 5678 numbers of dominant frequencies greater than or equal to 250 KHz and less than 350 KHz (medium frequency), and 459 numbers of dominant frequencies greater than 350 KHz (high frequency); and after calculating a number ratio of the five dominant frequency bands, visualizing a pie chart of dominant frequency distribution of the rocks; and sub-step 1315: according to the dominant frequency distribution map, the median dominant frequency, the average dominant frequency and the pie chart of dominant frequency distribution, the spectrum rule of rock burst can be roughly summarized as follows:

① The dominant frequencies are mainly distributed in the three distribution intervals of greater than or equal to 50 KHz and less than 150 KHz, greater than or equal to 150 KHz and less than 250 KHz, and greater than or equal to 250 KHz and less than 350 KHz; the dominant frequencies are most distributed in the interval greater than or equal to 50 KHz and less than 150 KHz, followed by the intervals greater than or equal to 250 KHz and less than 350 KHz, greater than or equal to 150 KHz and less than 250 KHz, and the distribution is least in the two parts less than 50 KHz and greater than or equal to 350 KHz.

② The dominant frequency values of acoustic emission signals of rock burst are mostly distributed in the three parts of "medium-low frequency—medium frequency—medium-high frequency"; on the whole, the dominant frequency of rock burst presents the evolution law of "medium-low frequency—medium frequency—medium-high frequency—medium frequency".

Further, in step 13, extracting the amplitude/energy characteristics of the rock data includes:

sub-step 1321: according to the "Dominant frequency.TXT" file that the first column is the real-times of occurrence time of rock burst, the second column is the maximum dominant frequency values extracted from the whole rock burst process by fast Fourier transform and the third column is the maximum amplitude values extracted from the whole rock burst process by fast Fourier transform, taking the time series in the first column of the "Dominant frequency.TXT" file as the X axis and a dominant frequency series in the third column of the "Dominant frequency.TXT" file as the Y axis, and making a line chart to obtain an acoustic emission amplitude diagram of marble;

sub-step 1322: according to the theorem, it is known that any vibrating object has energy, and its energy can be calculated by the following formulas:

assuming that the particle (mass point) density is p, the end coordinate is x, the displacement of the particle during vibration is y, w is the angular velocity, u is the wave velocity and A is the amplitude:

the vibration equation of particle is:

$$y = A\cos w\left(t - \frac{x}{u}\right);\quad (1)$$

the velocity of the vibrating particle can be obtained as follows:

$$v = \frac{\partial y}{\partial x} = -wA\sin\left(t - \frac{x}{u}\right);\quad (2)$$

the kinetic energy of volume element is:

$$E_k = \frac{1}{2}(\Delta m)v^2 = \frac{1}{2}\rho(\Delta v)A^2 w^2 \sin^2 w\left(t - \frac{x}{u}\right);\quad (3)$$

the potential energy of volume element is:

$$E_P = \frac{1}{2}k(\Delta y)2 = \frac{1}{2}\rho(\Delta v)A^2 w^2 \sin^2\left(t - \frac{x}{u}\right);\quad (4)$$

and, the mechanical energy of the particle is:

$$E = E_k + E_p = \rho(\Delta v)A^2 w^2 \sin^2\left(t - \frac{x}{u}\right);\quad (5)$$

where Δv is the volume of volume element, Δm is the mass of volume element, and k is the stiffness coefficient, and the conclusion 1 may be deduced that the level of acoustic energy is proportional to the square of sound amplitude;

The conclusion 1 shows that there is a potential relationship between rock energy and amplitude, and the higher the amplitude, the greater the energy; moreover, the energy in the early and middle stages of rock burst process is small, while the energy in the later stage of rock burst process increases sharply, and there is a sharp drop in energy when the rock burst occurs; and sub-step 1323: according to the "Dominant frequency.TXT" file that the first column is the real-time times of occurrence time of rock burst, the second column is the maximum dominant frequency values extracted from the whole rock burst process by fast Fourier transform and the third column is the maximum amplitude values extracted from the whole rock burst process by fast Fourier transform, taking the time series in the first column of the "Dominant frequency.TXT" file as the X axis, the dominant frequency series in the second column of the "Dominant frequency.TXT" file as the Y axis, and the dominant frequency series in the third column of the "Dominant frequency.TXT" file as the Z axis, and depicting a three-dimensional dominant frequency amplitude diagram of acoustic emission characteristics in rock burst experiment.

The conclusions are as follows:

① the amplitude of the whole rock burst process changes little in the early and middle stages, but suddenly increases in the later stage of rock burst process;

② from the conclusion 1, it can be concluded that the energy in the early and middle stages of rock burst process is small, while the energy in the later stage of rock burst process increases sharply, and there is a sharp drop in energy when the rock burst occurs;

③ the dominant frequency intervals of acoustic emission signals during rock burst are concentrated in three parts: medium and low frequency, medium frequency and medium and high frequency, and the dominant frequency characteristics show the evolution law of "medium and low frequency→medium frequency→medium and high frequency→medium frequency"; especially at the rock burst time, the acoustic emission spectrum is characterized by high amplitude of medium frequency; and ④ in the early and middle stages of rock burst, the amplitude and energy change little, while in the later stage of rock burst, the dominant frequency at the time of rock burst mainly concentrates in the medium frequency band (150 KHz-250 KHz) distribution interval, where the amplitude suddenly increases and then rapidly decreases. Therefore, it can be seen that the rock burst has low energy at the early stage, and then the energy decreases; the rock burst energy rises sharply at the later stage, and then decreases sharply, and the acoustic emission spectrum at this time is characterized by high amplitude of medium frequency.

Further, S2 specifically includes:

step 21, acquiring the spectrum characteristics and the amplitude/energy characteristics of rock data; and step 22, according to the spectrum characteristics and the amplitude/energy characteristics, accurately predicting the rock burst by the K-nearest neighbour algorithm.

Further, accurately predicting the rock burst by the K-nearest neighbour algorithm includes:

sub-step 221: according to the "Dominant frequency.TXT" file that the first column is the real-time times of occurrence time of rock burst, the second column is the maximum dominant frequency values extracted from the whole rock burst process by fast Fourier transform and the third column is the maximum amplitude values extracted from the whole rock burst process by fast Fourier transform, in order to ensure the prediction effect of the prediction model, standardizing the maximum dominant frequency values in the second column and the maximum amplitude values in the third column in the "Dominant frequency.TXT" file to normalize as data of 0-1 as per a formula as follows:

$$X^* = \frac{X - X_{min}}{X_{max} - X_{min}}, \quad (6)$$

in which: X is the desired characteristic value, $X^*$ is the standardized value of the desired characteristic value, $X_{min}$ is the minimum value in the characteristic class, and $X_{max}$ is the maximum value in the characteristic class;

sub-step 222: on the basis of data normalization, using dominant frequency and amplitude data of acoustic emission as input characteristic data, and using the results of indicating rock burst occurred or not obtained by automatic identification and labeling algorithms as classification labels, that is, taking the labels of data in the occurrence time of rock burst in a process of rock burst experiment as 1, and taking labels of the other data in a time of without rock burst as 0; and sub-step 223, on the basis of the processed data, dividing the size of the data set into training set and test set according to the ratio of 9:1, and training the prediction model with K-nearest neighbor algorithm to accurately predict rock burst. Accuracy is used to evaluate the quality of the classification model, and the accuracy represents the percentage of the correct prediction results in the total sample; recall indicates the probability of being predicted as a positive sample in the actual positive samples; and F1 value (the harmonic average of accuracy and recall) is a statistical quantity, which is numerically equal to the harmonic average of accuracy and recall, and it is also often used to evaluate the quality of the model; the K-nearest neighbor algorithm is used to apply these three characteristics to the processed data, and the data are calculated and analyzed.

Figure 2:
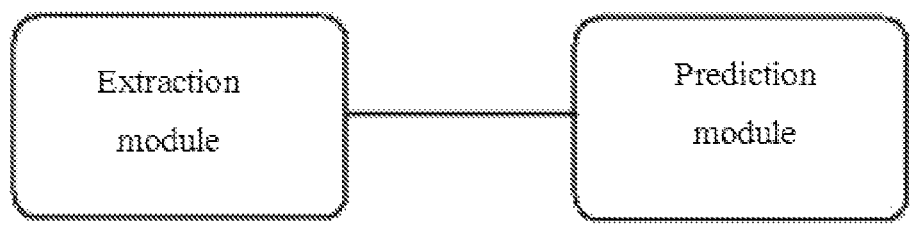
FIG. 2 is a structural schematic diagram of the K-nearest neighbour rock burst prediction device based on big data visualization analysis according to the invention.

As shown in FIG. 2, the invention provides a K-nearest neighbour rock burst prediction device based on big data visualization analysis for realizing the K-nearest neighbour rock burst prediction method based on big data visualization analysis, and the device includes:

an extraction module, which is used for obtaining the spectrum characteristics and amplitude/energy characteristics of rocks according to rock data; and a prediction module, which is used for accurately predicting the rock burst through the K-nearest neighbour algorithm according to the spectrum characteristics and the amplitude/energy characteristics. In an exemplary embodiment, the extraction module and the prediction module are software modules stored in one or more memories and executable by one or more processors coupled to the one or memories.

Example 1: Rock Burst Prediction of Laizhou Granite step 1, applying the prediction method according to the invention to the actual rock burst prediction of Laizhou granite, and as per the step of extracting frequency domain of rock data, extracting the frequency domain-amplitude values of Laizhou granite rock data, namely the frequency domain data of Laizhou granite rock data;

step 2, according to the frequency domain data of rock data and the method of extracting the spectrum characteristics of rock data, extracting the spectrum characteristics of Laizhou granite; and obtaining the dominant frequency distribution map of Laizhou granite and pie chart of dominant frequency distribution of Laizhou granite respectively;

according to the dominant frequency distribution map of Laizhou granite, the pie chart of Laizhou granite dominant frequency distribution and the data analysis and calculation of dominant frequency values, obtaining the rock burst law of Laizhou granite that the dominant frequency distribution interval of sound signals in the rock burst process is mainly distributed in the three parts of "medium and low frequency, medium frequency and medium and high frequency"; on the whole, the dominant frequency characteristics show the evolution law of "medium and low frequency→medium frequency→medium and high frequency→medium frequency";

step 3: according to the frequency domain data of rock data and the method of extracting the amplitude/energy characteristics of rock data, extracting the amplitude-energy characteristics of Laizhou granite; and obtaining the acoustic emission amplitude diagram and three-dimensional dominant frequency amplitude diagram of Laizhou granite respectively; according to the acoustic emission amplitude diagram and three-dimensional dominant frequency amplitude diagram of Laizhou granite, it can be concluded that the rock burst law/rule of Laizhou granite is a change law that the dominant frequency amplitude energy experiences "gradually increasing→gradually decreasing→sharply increasing→sharply decreasing"; and step 4, according to the spectrum characteristics and the amplitude/energy characteristics, and the accurate prediction part of rock burst made by K-nearest neighbour algorithm, predicting and analyzing rock burst of Laizhou granite by K-nearest neighbour (KNN) algorithm, and gaining the following algorithm effects.

The algorithm effects are shown in Table 1.

TABLE 1

| Model | Accuracy | Recall | F1 |
| --- | --- | --- | --- |
| KNN | 96.687% | 81.899% | 88.681% |

As can be seen from Table 1, the prediction accuracy of the KNN rock burst prediction algorithm according to the invention for Laizhou granite is as high as 96.687%, that is, the ratio of the correct times of rock burst events predicted by this model to the total number of rock burst events is 96.687%; at the same time, the recall rate of the model is 81.899%, and the F1 value is 88.681%.

From the above data and results, it can be concluded that the model has good performance in rock burst predicting, and the model not only has high prediction accuracy, but also can be used for rock burst prediction of other kinds of rocks.

It should be understood that although this specification is described in terms of embodiments, not every embodiment only contains an independent technical solution. This description of the specification is only for clarity. Those skilled in the art should take the specification as a whole, and the technical solutions in respective embodiments may be appropriately combined to form other embodiments that can be understood by those skilled in the art.

What is claimed is:

1. A K-nearest neighbour rock burst prediction method based on big data visualization analysis, comprising:
    S1, obtaining spectrum characteristics and amplitude/energy characteristics of rocks according to rock data; and
    S2, predicting rock burst by a K-nearest neighbour (KNN) algorithm according to the spectrum characteristics and amplitude/energy characteristics;
    wherein, S1 specifically comprises:
        step 11, acquiring the rock data;
        step 12, performing Fourier transform on time domain data of the rock data to obtain frequency domain data of the rock data; and
        step 13, extracting the spectrum characteristics and the amplitude/energy characteristics of the rock data according to the frequency domain data of the rock data;
    wherein in the step 13, the extracting the spectrum characteristics of the rock data comprises:
        sub-step 1311, obtaining real-time times of occurrence time of rock burst according to the frequency domain data of the rock data, and storing the real-time times in a "Dominant frequency.TXT" file in turn, wherein in the "Dominant frequency.TXT" file, a first column is the real-time times of occurrence time of rock burst, a second column is maximum dominant frequency values extracted from a whole rock burst process by fast Fourier transform, and a third column is maximum amplitude values extracted from the whole rock burst process by fast Fourier transform;
        sub-step 1312: taking a time series in the first column of the "Dominant frequency.TXT" file as an X axis and a dominant frequency series in the second column of the "Dominant frequency.TXT" file as a Y axis, and making a scatter plot to obtain a dominant frequency distribution map;
        sub-step 1313: analyzing data of the "Dominant frequency.TXT" file to obtain a median dominant frequency of 84.472 KHz and an average dominant frequency of 134.410 KHz;
        sub-step 1314, dividing dominant frequencies into five dominant frequency bands according to the dominant frequency distribution map, wherein the five dominant frequency bands respectively are a low frequency band with dominant frequencies less than 50 KHz, a medium-low frequency band with dominant frequencies greater than or equal to 50 KHz and less than 150 KHz, a medium frequency band with dominant frequencies greater than or equal to 150 KHz and less than 250 KHz, a medium-high frequency band with dominant frequencies greater than or equal to 250 KHz and less than 350 KHz, and a high frequency band with dominant frequencies greater than 350 KHz; there are 203 numbers of dominant frequencies less than 50 KHz, 18464 numbers of dominant frequencies at 50 KHz-150 KHz, 1149 numbers of dominant frequencies at 150 KHz-250 KHz, 5678 numbers of dominant frequencies at 250 KHz-350 KHz, and 459 numbers of dominant frequencies greater than 350 KHz; and after calculating a number ratio of the five dominant frequency bands, visualizing a dominant frequency distribution pie chart of the rocks; and
        sub-step 1315: obtaining a spectrum rule of rock burst according to the dominant frequency distribution map, the median dominant frequency, the average dominant frequency and the dominant frequency distribution pie chart.

2. The K-nearest neighbour rock burst prediction method based on big data visualization analysis according to claim 1, wherein in the step 12, the obtain frequency domain data of the rock data comprises:
    sub-step 121: parsing the rock data to obtain parsed waveform file data;
    sub-step 122, extracting the parsed waveform file data, and sorting the waveform file data according to a time sequence of rock burst occurrence; and
    sub-step 123: performing fast Fourier transform on the sorted waveform file data to obtain frequency domain-amplitude values as the frequency domain data of the rock data.

3. The K-nearest neighbour rock burst prediction method based on big data visualization analysis according to claim 1, wherein S2 specifically comprises:
    step 21, acquiring the spectrum characteristics and the amplitude/energy characteristics of the rock data; and
    step 22, accurately predicting the rock burst by the K-nearest neighbor algorithm based on the spectrum characteristics and the amplitude/energy characteristics.

4. The K-nearest neighbour rock burst prediction method based on big data visualization analysis according to claim 1, wherein the S2 specifically comprises: standardizing the maximum dominant frequency values in the second column and the maximum amplitude values in the third column of the "Dominant frequency.TXT" file as per a formula to thereby normalize as data of 0-1, according to the "Dominant frequency.TXT" file that the first column is the real-time times of occurrence time of rock burst, the second column is the maximum dominant frequency values extracted from the whole rock burst process by fast Fourier transform and the third column is the maximum amplitude values extracted from the whole rock burst process by fast Fourier transform; wherein the formula is as follows:

$$X^* = \frac{X - X_{min}}{X_{max} - X_{min}},$$

where X is a desired characteristic value, $X^*$ is a standardized value of the desired characteristic value, $X_{min}$ is a minimum value in a characteristic class which the desired characteristic value belongs to, and $X_{max}$ is a maximum value in the characteristic class;
wherein on the basis of data normalization, dominant frequency and amplitude data of acoustic emission are used as input characteristic data, and results of indicating rock burst occurred or not obtained by automatic identification are used as classification labels, in which labels of data in the occurrence time of rock burst during a process of rock burst experiment are taken as 1, and labels of data in non-occurrence time of rock burst during the process of rock burst experiment are taken as 0.

* * * * *